(12) United States Patent
Daly et al.

(10) Patent No.: US 8,515,544 B2
(45) Date of Patent: *Aug. 20, 2013

(54) COCHLEAR IMPLANT EXTERNAL COMPONENT HAVING A MOVABLE ANTENNA

(75) Inventors: Christopher Newton Daly, Bilgola Plateau (AU); Akira Nakazawa, Balmain (AU); Peter Scott Single, Lane Cove (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/018,976

(22) Filed: Feb. 1, 2011

(65) Prior Publication Data

US 2011/0137377 A1 Jun. 9, 2011

Related U.S. Application Data

(62) Division of application No. 10/506,331, filed as application No. PCT/AU03/00281 on Mar. 10, 2003, now Pat. No. 7,881,800.

(30) Foreign Application Priority Data

Mar. 8, 2002 (AU) .................................. PS 0976
Mar. 8, 2002 (AU) .................................. PS 0977

(51) Int. Cl.
*A61N 1/18* (2006.01)
(52) U.S. Cl.
USPC ........................................................ 607/55

(58) Field of Classification Search
USPC ...................................... 607/55–57; 381/330
See application file for complete search history.

(56) References Cited

U.S. PATENT DOCUMENTS 4,453,050 A * 6/1984 Enokido ........................ 381/381
4,611,598 A * 9/1986 Hortmann et al. ............... 607/57
(Continued)

FOREIGN PATENT DOCUMENTS
WO WO-03076012 9/2003

OTHER PUBLICATIONS

International Preliminary Examination Report issued in connection with International Application No. PCT/AU03/00281, Jul. 28, 2004, 5 pages.

(Continued)

*Primary Examiner* — Scott Getzow
*Assistant Examiner* — Amanda Patton
(74) *Attorney, Agent, or Firm* — Kilpatrick, Townsend & Stockton, LLP.

(57) ABSTRACT

An external component of a cochlear implant system. The external component includes a support configured to house one or more electronic components and to be mounted to an outer ear of a recipient, and an external antenna configured to provide one or more of power and data signals from the electronic components to an implantable component of the cochlear implant system, wherein the external antenna is mounted to the support such that the external antenna moveable relative to at least a portion of the support.

19 Claims, 11 Drawing Sheets

(56) References Cited

U.S. PATENT DOCUMENTS

| | | | |
|---|---|---|---|
| 6,141,591 A * | 10/2000 | Lenarz et al. | 607/57 |
| 6,161,046 A | 12/2000 | Maniglia et al. | |
| 6,178,353 B1 | 1/2001 | Griffith et al. | |
| 6,205,360 B1 | 3/2001 | Carter et al. | |
| 6,246,911 B1 | 6/2001 | Seligman | |
| 6,272,382 B1 * | 8/2001 | Faltys et al. | 607/57 |
| 6,308,101 B1 | 10/2001 | Faltys et al. | |
| 6,648,914 B2 | 11/2003 | Berrang | |
| 7,881,800 B2 * | 2/2011 | Daly et al. | 607/57 |

OTHER PUBLICATIONS

International Search Report issued in connection with International Application No. PCT/AU03/00281, Apr. 29, 2003, 4 pages.

Written Opinion issued in connection with International Application No. PCT/AU03/00281, Oct. 8, 2003, 5 pages.

* cited by examiner

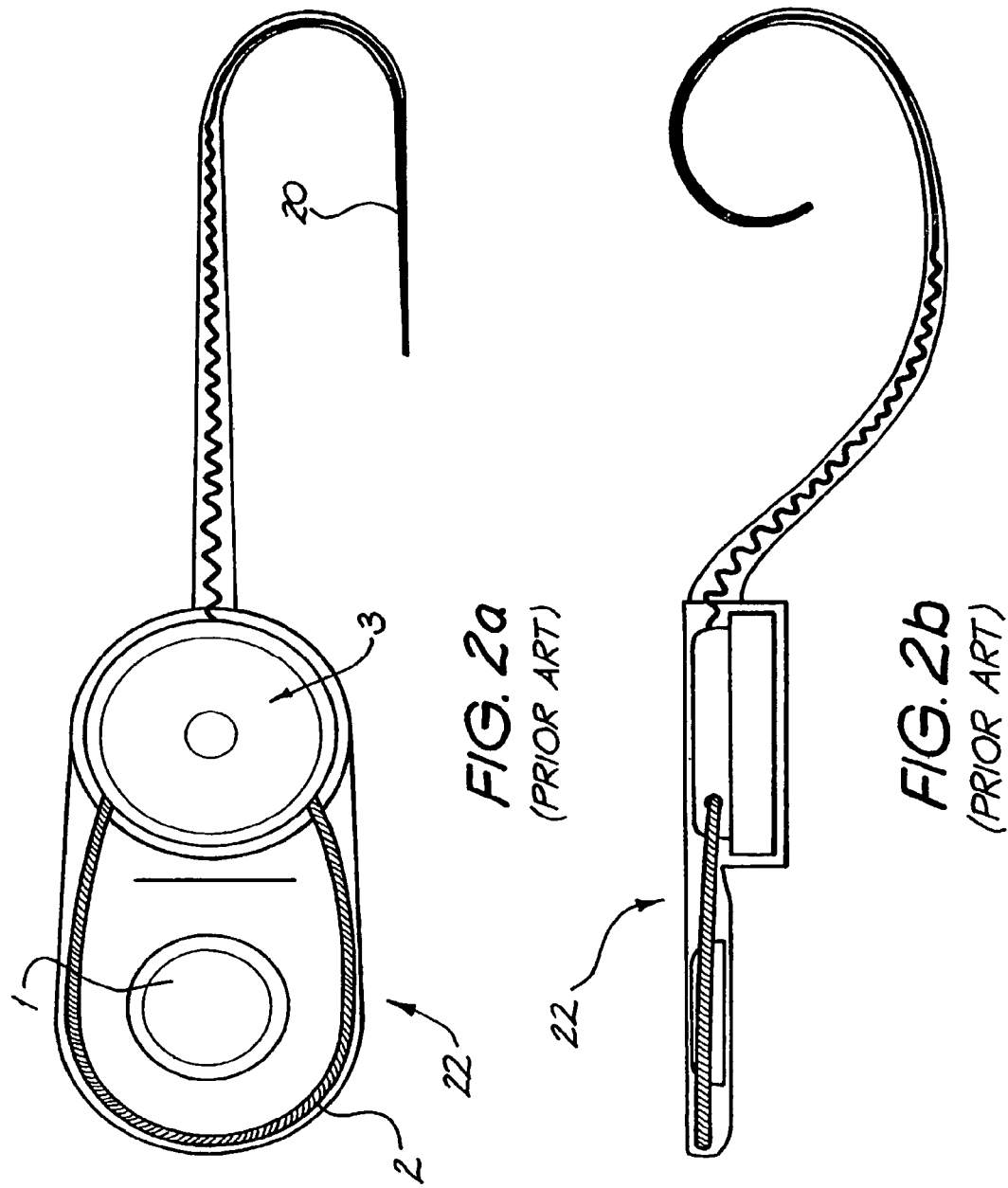

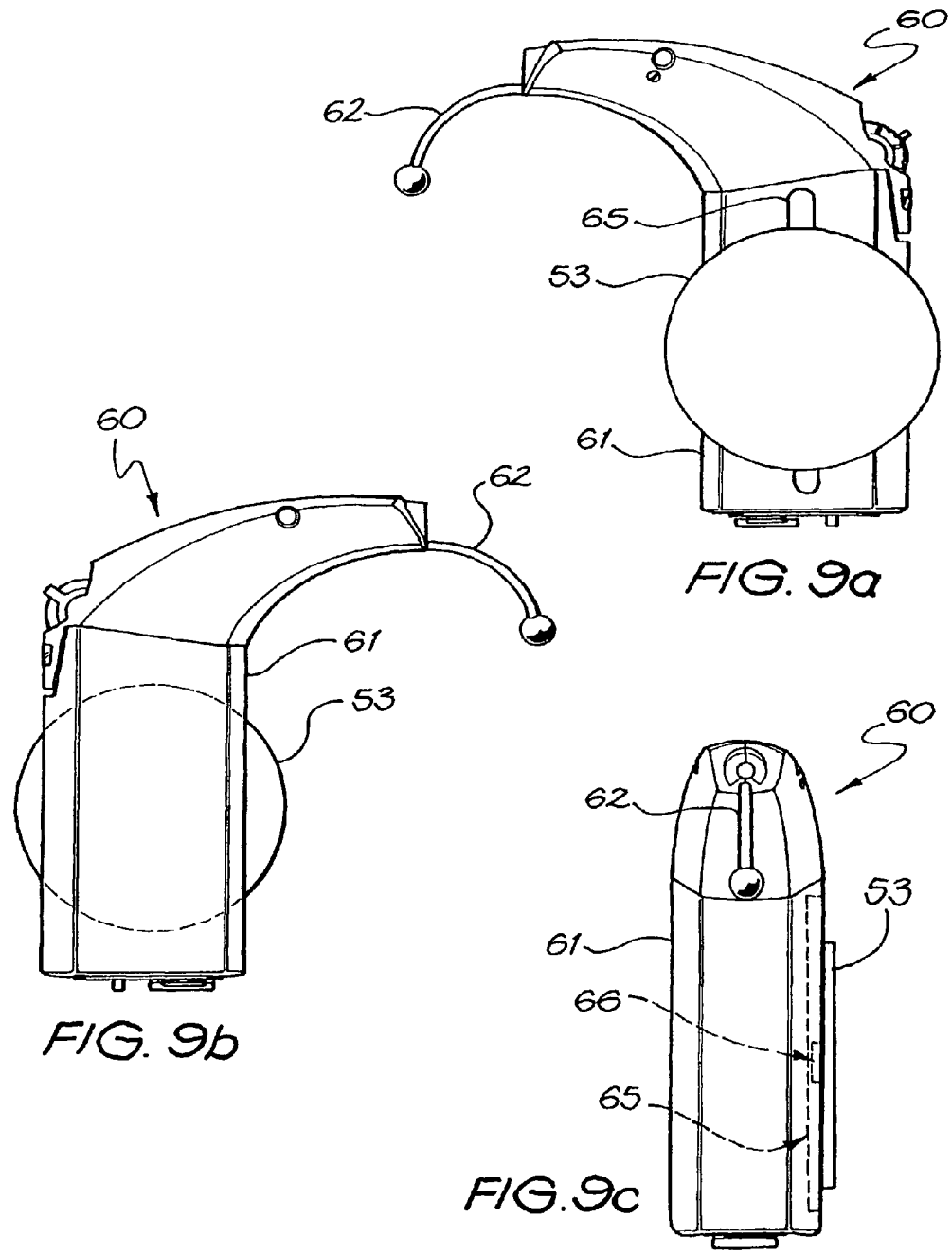

COCHLEAR IMPLANT EXTERNAL COMPONENT HAVING A MOVABLE ANTENNA

CROSS-REFERENCE TO RELATED APPLICATIONS

This application is a Divisional of U.S. patent application Ser. No. 10/506,331, filed on Sep. 2, 2004, which is a national stage application of International Application No. PCT/AU2003/000281, filed on Mar. 10, 2003, which claims priority from Australian Provisional Patent Application No. PS 0976, filed on Mar. 8, 2002, and Australian Provisional Patent Application No. PS 0977, filed on Mar. 8, 2002. Each of these documents is hereby incorporated by reference herein in its entirety.

BACKGROUND

1. Field of the Invention

The present invention relates to a cochlear implant system. In one aspect, the present invention relates to a cochlear implant system that can be used with or without a magnetic alignment system for the transmitter and receiver coils of the system. In another aspect, the invention relates to an external component of a cochlear implant system that is constructed in a manner that facilitates alignment of the external transmitter coil with an implanted receiver coil.

2. Related Art

In many people who are profoundly deaf, the reason for deafness is absence of, or destruction of, the hair cells in the cochlea which transduce acoustic signals into nerve impulses. These people are unable to derive suitable benefit from conventional hearing aid systems, no matter how loud the acoustic stimulus is made, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930 provides a description of one type of traditional cochlear implant system.

Typically, cochlear implant systems have consisted of essentially two components, an external component commonly referred to as a processor unit and an internal implanted component commonly referred to as a receiver/stimulator unit. Traditionally, both of these components have cooperated together to provide the sound sensation to a user.

The external component has traditionally consisted of a microphone for detecting sounds, such as speech and environmental sounds, a speech processor that converts the detected sounds, particularly speech, into a coded signal, a power source such as a battery, and an external transmitter coil.

The coded signal output by the speech processor is transmitted transcutaneously to the implanted receiver/stimulator unit situated within a recess of the temporal bone of the user. This transcutaneous transmission occurs via the external transmitter coil which is positioned to communicate with an implanted receiver coil provided with the receiver/stimulator unit.

This communication serves two essential purposes, firstly to transcutaneously transmit the coded sound signal and secondly to provide power to the implanted receiver/stimulator unit. Conventionally, this link has been in the form of a radio frequency (RF) link, but other such links have been proposed and implemented with varying degrees of success.

The implanted receiver/stimulator unit traditionally includes a receiver coil that receives the coded signal and power from the external processor component, and a stimulator that processes the coded signal and outputs a stimulation signal to an intracochlear electrode assembly which applies the electrical stimulation directly to the auditory nerve producing a hearing sensation corresponding to the original detected sound.

Traditionally, the external componentry has been carried on the body of the user, such as in a pocket of the user's clothing, a belt pouch or in a harness, while the microphone has been mounted on a clip behind the ear or on the lapel of the user.

More recently, due in the main to improvements in technology, the physical dimensions of the speech processor have been able to be reduced allowing for the external componentry to be housed in a small unit capable of being worn behind the ear of the user. This unit allows the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit.

The external transmitter coil has traditionally been held in place via a magnet which aligns with a magnet or an appropriate ferromagnetic material positioned within the internal receiver coil through magnetic attraction. Such a secure alignment ensures that both coils are coupled efficiently so that the transfer of data and power is effectively performed. Whilst aiding in proper coil alignment, such a connection also provides a firm and secure method of holding the external coil in position on the head of the user, with the strength of this securing force being adjustable through the use of variable strength magnets in the external coil, This method of securing the external and internal coils in close alignment is important for children and the like who are active and mobile and as such require a simple, yet effective means of ensuring that alignment of the coils is maintained.

Early devices attempted to facilitate alignment of the internal and external coils through a headband arrangement that was fitted around the head of the user to hold the coil in place. Such an arrangement proved troublesome as it could easily be knocked or unintentionally adjusted, especially with small children, and as such communication could easily be lost or reduced between the external device and the implant. Such an arrangement was also not aesthetically pleasing.

A downside of the present system is the fact that for some people, the external coil is quite visible and cannot be easily hidden and as such they are conscious of the fact that their device is noticeable to others. It is, therefore, highly desirable to provide a system wherein the external components are relatively comfortable and easily worn so that the user does not feel self-conscious wearing the device.

Another issue with prior art devices is the fact that the magnet used to facilitate and maintain proper alignment of the coils, prevents, or is detrimental to the effective use of magnetic resonance imaging (MRI) techniques, in the head region surrounding the implanted magnet. The presence of the magnet in such instances can distort the image taken from such a technique and in some instances the technique may even cause the implanted magnet to move, causing problems with the implanted device. Therefore it would be highly desirable to provide an implant that allows recipients to utilise such a valuable medical diagnostic tool as an MRI, and ensure that such a procedure can be undergone without the risk of damage to the recipient and/or their device.

In order to overcome these disadvantages magnetless cochlear implants have been proposed, such as that disclosed in U.S. Pat. No. 6,141,591. This patent discloses an implant that is strategically positioned via a set of alignment tools so that it can be aligned to communicate with an external controller/transmitter without the need for a magnet. The method of implantation requires a set of specific steps to ensure that the device is embedded into the skull at the appropriate position, so that in use, the implant coil communicates with an external coil incorporated in an external unit worn behind the ear of the recipient. One problem with this particular device and method is that it requires the implant to be implanted to a high degree of accuracy that is not readily achievable in a surgical environment when dealing with soft tissue and the like and anatomical variations from recipient to recipient. As such, it is difficult to ensure the implant is positioned in the correct place. Still further, should there be a change in the head shape, such as that which occurs during a child's growth, the implant may be placed such that the alignment with the external unit is not possible nor ideal.

In any regard, it is important that the actual site of location of the device is chosen by the surgeon to ensure safety and conformity to the recipient's natural physiology. In actual fact, the final location of the device does differ from recipient to recipient and this can be due to a number of reasons, such as surgeon preference, skin thickness, and bone strength and porosity. It is, therefore, important that a cochlear implant be constructed such that there is at least some degree of freedom of positioning of the device during surgery.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY

In one aspect of the present invention, an external component of a cochlear implant system is disclosed. The external component comprises a support configured to house one or more electronic components and to be mounted to an outer ear of a recipient, and an external antenna configured to provide one or more of power and data signals from the electronic components to an implantable component of the cochlear implant system, wherein the external antenna is mounted to the support such that the external antenna moveable relative to at least a portion of the support.

In another aspect of the present invention, cochlear implant system is disclosed. The cochlear implant system comprises an implantable component comprising a receiver coil, and an external component. The external component comprises a support configured to house one or more electronic components and to be mounted to an outer ear of a recipient, and an external antenna configured to provide one or more of power and data signals from the electronic components to the receiver coil, wherein the external antenna is mounted to the support such that the external antenna moveable relative to at least a portion of the support.

In yet another aspect of the present invention, a method of adjusting a cochlear implant system is disclosed. The cochlear implant system comprises an implantable component and an external component, the implantable component including an implantable housing and a receiver coil, and the external component including a support and an external antenna mounted to the support. The method comprises moving the external antenna relative to at least a portion of the support such that, when the external component is mounted to a recipient's outer ear, the external antenna is substantially aligned with the receiver coil implanted in the recipient, and locking the external antenna to the support, using a locking mechanism, to prevent the external antenna from moving relative to the support.

BRIEF DESCRIPTION OF THE DRAWINGS

By way of example only, a preferred embodiment of the invention is now described with reference to the accompanying drawings, in which:

FIGS. 2a and 2b are plan and side elevation views, respectively, of a prior art implantable component of a cochlear implant system;

FIGS. 8a-c and 9a-c depict various arrangements of external components according to the present invention.

DETAILED DESCRIPTION

Embodiments of the present invention provide a cochlear implant system that is adapted to address the above deficiencies of the prior art.

There are instances where a conventional magnetic alignment system is the most desirable option for use by a recipient of a cochlear implant system. Children and active adult recipients do however, require a system that can be altered as the needs of the recipient change.

In the case of young children, it has been found that a behind-the-ear (BTE) device is not always an ideal solution as the ear may not be sufficiently large enough to support such a unit comfortable and securely. In such instances, a magnet coil is still far more beneficial to transmit data and energy to the implant, however as the child develops and grows to an age where system invisibility is important, there is often a desire from such recipients to be provided with the option for a less visible device.

Further to this, the choice of whether a magnetic alignment system is used or whether a less visible system is employed, remains the choice of the recipient. In this regard, it is important that the recipient has access to all such options, with the options not being limited by the design of the particular implant. Traditional commercially available implants have been designed such that they can only be implanted in a particular orientation, with that orientation being dictated by the location of the exit point of the electrode array with respect to the implant package. Typically, the electrode array has exited the implant package at an end of the package closest to the cochleostomy formed by the surgeon. There is a need to provide a device that can be implanted in a number of orientations dependant upon the choice of the recipient.

The present invention offers the ability to provide a cochlear implant system that can operate in a conventional manner that utilizes a magnetic connection to maintain the coils in alignment, and with a relatively minor procedure allows the device to be utilized in a magnetless manner. More specifically, the present invention provides a cochlear implant system that is designed in such a way as to allow the implant to be altered in orientation so that instead of alignment with the coils occurring through a magnetic connection, the implanted coil can directly communicate with a unit worn behind the ear of the recipient without the need for use of such magnets.

The present invention also offers the ability to provide a cochlear implant system that can operate in a conventional manner utilizing a magnetic connection to maintain the coils in alignment, or can operate in a magnetless manner where the implanted coil can directly communicate with a unit worn behind the ear of the recipient without the need for the use of magnets.

Figure 1:
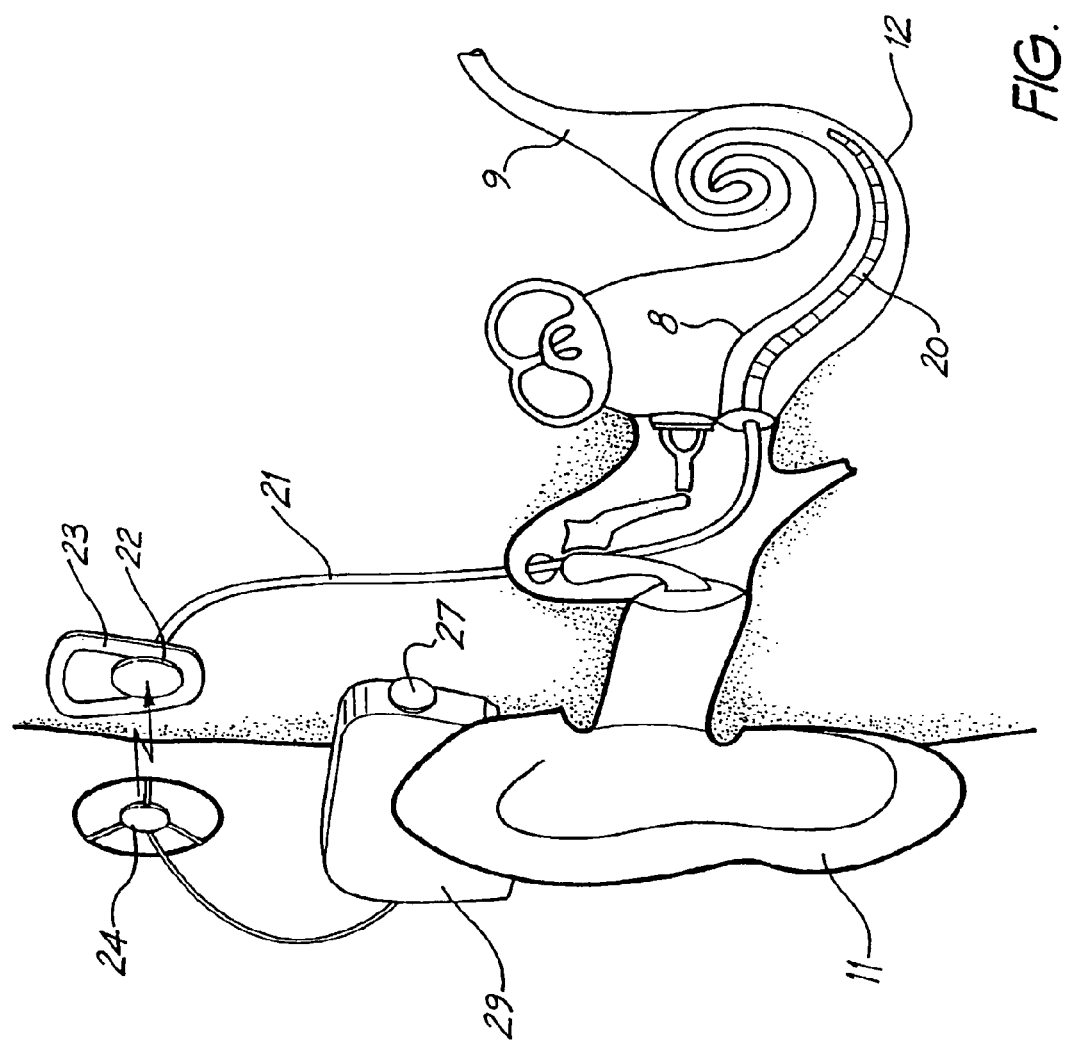
FIGS. 1 and 5 are pictorial representation of one example of a prior art cochlear implant system.

A simplified conventional cochlear implant is shown in FIG. 1. Cochlear implants typically consist of two main components, an external component including a speech processor 29, and an internal component including an implanted receiver and stimulator unit 22. The external component includes an on-board microphone 27. The speech processor 29 is, in this illustration, constructed and arranged so that it can fit behind the outer ear 11. Alternative versions may be worn on the body. Attached to the speech processor 29 is a transmitter coil 24 which transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 thereby stimulating the auditory nerve 9. The operation of such a device is described, for example, in U.S. Pat. No. 4,532,930.

The sound processor 29 of the cochlear implant can perform a spectral analysis of the acoustic signals and outputs channel amplitude levels. The sound processor 29 can also sort the outputs in order of magnitude, or flag the spectral maxima as used in the SPEAK strategy developed by Cochlear Ltd.

Turning to FIG. 2, there is shown a more detailed depiction of a typical implanted stimulator unit 22. This unit includes a receiver/stimulator package 3 which contains the associated implant electronics that are capable of converting the received signals into stimulation patterns capable of delivery by the electrode array 20. A magnet 1 is positioned within the receiver coil 2 to assist in holding and aligning an external coil in alignment with the receiver coil 2 as previously discussed. As shown, the electrode array 20 exits from the receiver/stimulator package at one end of the device, typically the end remote from the receiver coil 2. The receiver stimulator package 3 is typically embedded and/or secured within the mastoid bone in a hole drilled by the surgeon which both acts as a securing well to maintain the device in place, and also as a means to reduce the volume of the device that extends beyond the bone of the recipient. As can be understood, the configuration of such a device is designed such that it remains in the implanted orientation for the life of the recipient, or at least until the device is removed. The orientation of this prior art device cannot be substantially changed.

An implantable component of a cochlear implant system according to the present invention is depicted generally as 30 in FIGS. 3a-d. The component 30 includes a receiver/stimulator package 31 and a receiver coil 32 attached thereto. A removable magnet 33 is positioned within the receiver coil 32 in much the same way as a conventional implant. In the present invention, however, the electrode array 20 exits the component substantially at a right angle to the longitudinal axis of the component 30.

In the embodiment shown in FIGS. 3a-d, the intra-cochlear array 20 exits from a first lower edge of the component 30 while the extra-cochlear array 38 exits from a second upper edge of the component 30. For clarity, the extra-cochlear and intracochlear electrode arrays are not always shown in their entirety in these figures, however it is understood that such electrodes are well known in the art and as such do not require further explanation in this application.

Figure 3A:
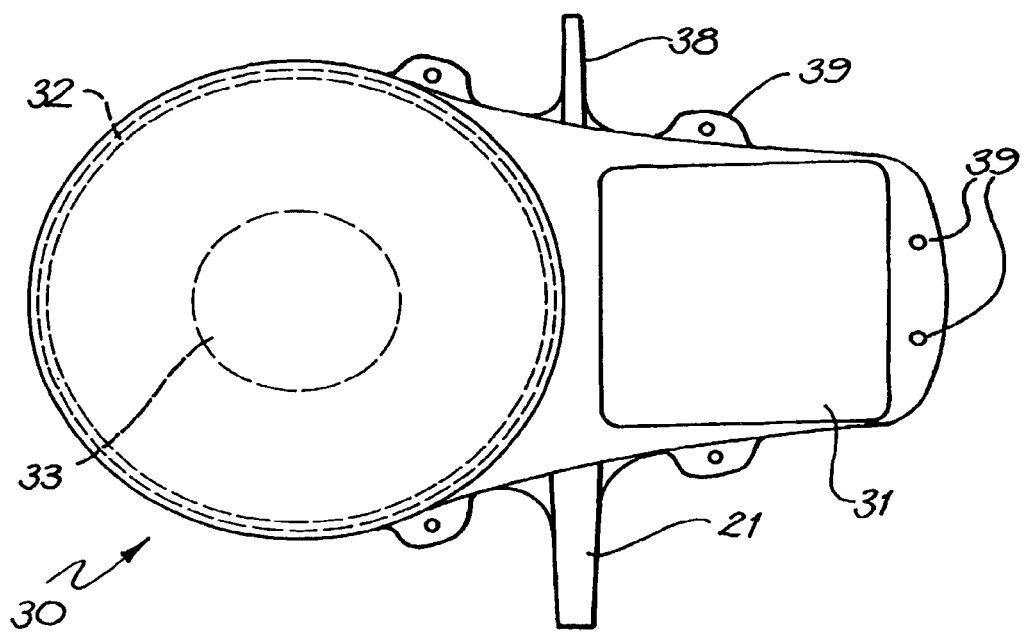
FIGS. 3a, 3b, 3c and 3d are plan and side elevation views, respectively, of embodiments of an implantable component of a cochlear implant system according to the present invention.
Figure 3B:
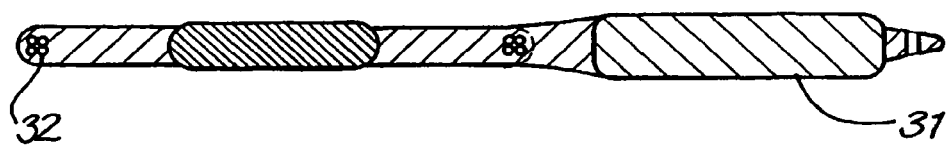
Figure 3C:
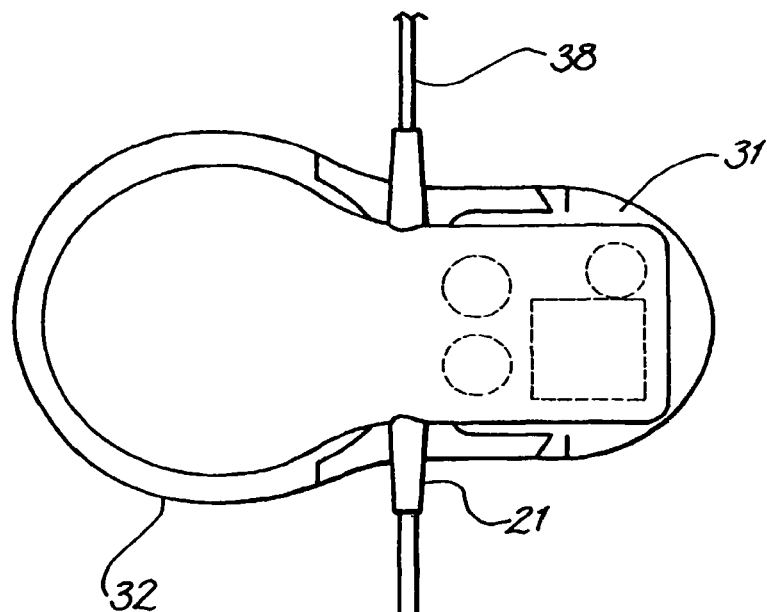
Figure 3D:
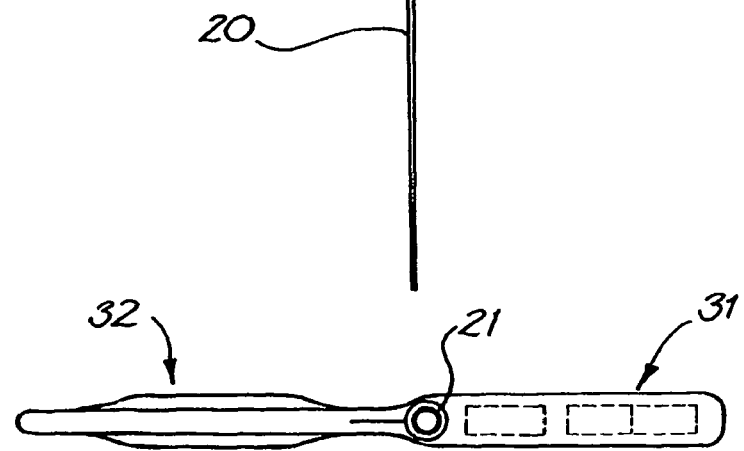

The orientation of the component 30 as depicted in FIG. 3a is representative of the orientation of the component 30 on implantation. In other words, the stimulator is preferably implanted such that the intra-cochlear electrode 20 exits on the lower first edge of the implant, towards the mastoid cavity.

The component 30 is also largely symmetric about a longitudinal and a lateral plane and considerably thinner than known implants. This allows for a relatively more straightforward implantation surgery where bone drilling is minimised and the component 30 can be positioned in any orientation with no surface necessarily requiring to be implanted "right side-up". As is shown most clearly in FIG. 3a, an optional feature may be to provide a number of tie down points 39 at strategic points on the component to stabilise and secure the component, resulting in both the initial implant surgery and any subsequent revision surgery being simpler and requiring less bone drilling than conventional surgeries. In this regard, it is envisaged that the device could be merely positioned under the skin without the need for any additional drilling to secure the component in place.

Further to this, due to the present implant having a larger flat surface area, compared to known solid ceramic case implants, the implant is easier to stabilise in position. The implant is therefore much more cosmetic, having a less prominent device requiring less bone drilling, and has increased robustness and reduced size and is therefore more suitable for implantation into very young children.

Further, when the recipient desires to convert the implant from one that relies on use of a magnet to one that does not, such as when a child matures to a stage when a BTE device can be reliably worn, the required revision surgery is relatively very simple.

Figure 4:
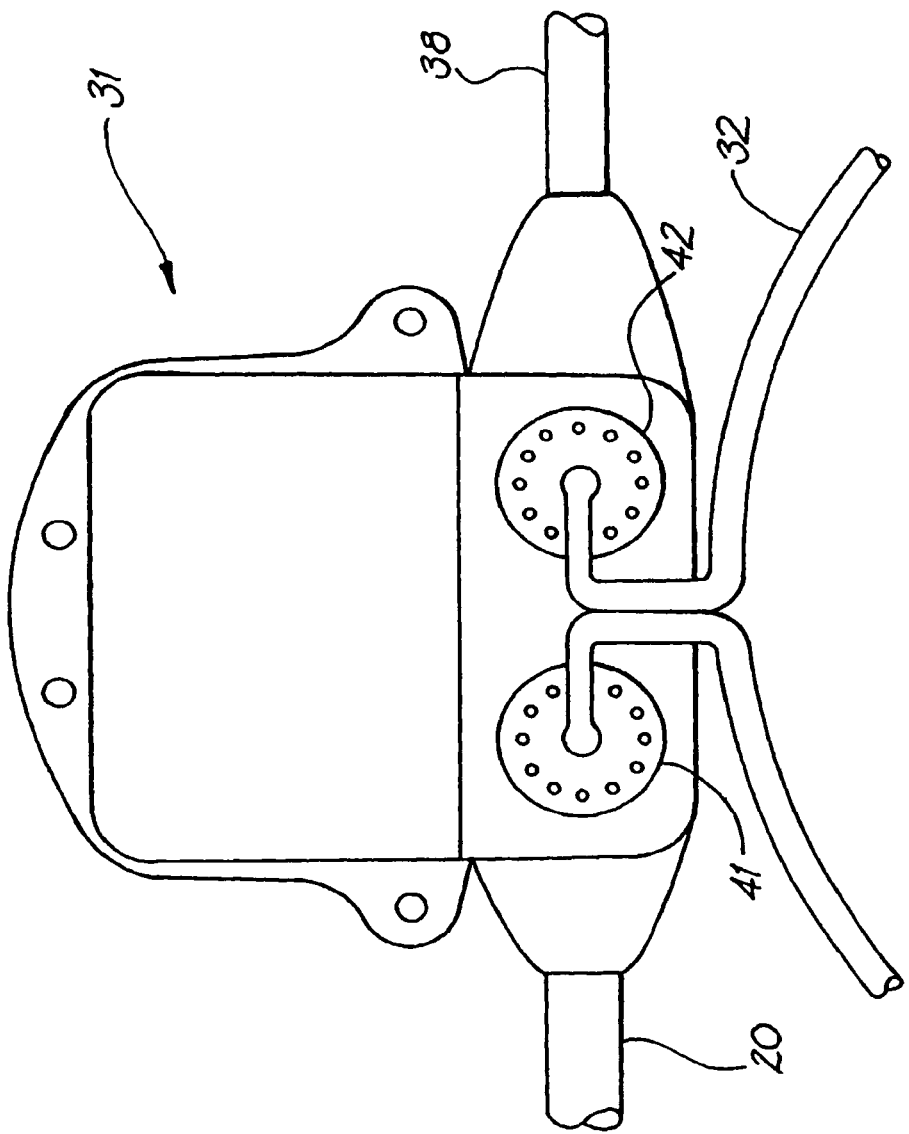
FIG. 4 is an underneath plan view of a portion of the implantable component of FIGS. 3a and 3b.

FIG. 4 shows in more detail the connection of the intra-cochlear electrode array 20, the extra-cochlear electrode array 38 and the receiver coil 32 to the receiver/stimulator package 31. The intra-cochlear electrode 20 in this embodiment has 22 electrodes which are connected to the implant circuitry contained within the stimulator receiver package 31 via two feedthrough devices 41 and 42. These feedthrough devices maintain hermeticity with the implant circuitry allowing direct connection with the wires connected to the electrode elements of the array and extending back to the implant circuitry. The coil and the lead of the extra-cochlear electrode array are also connected via these feedthroughs 41,42.

Figure 5:
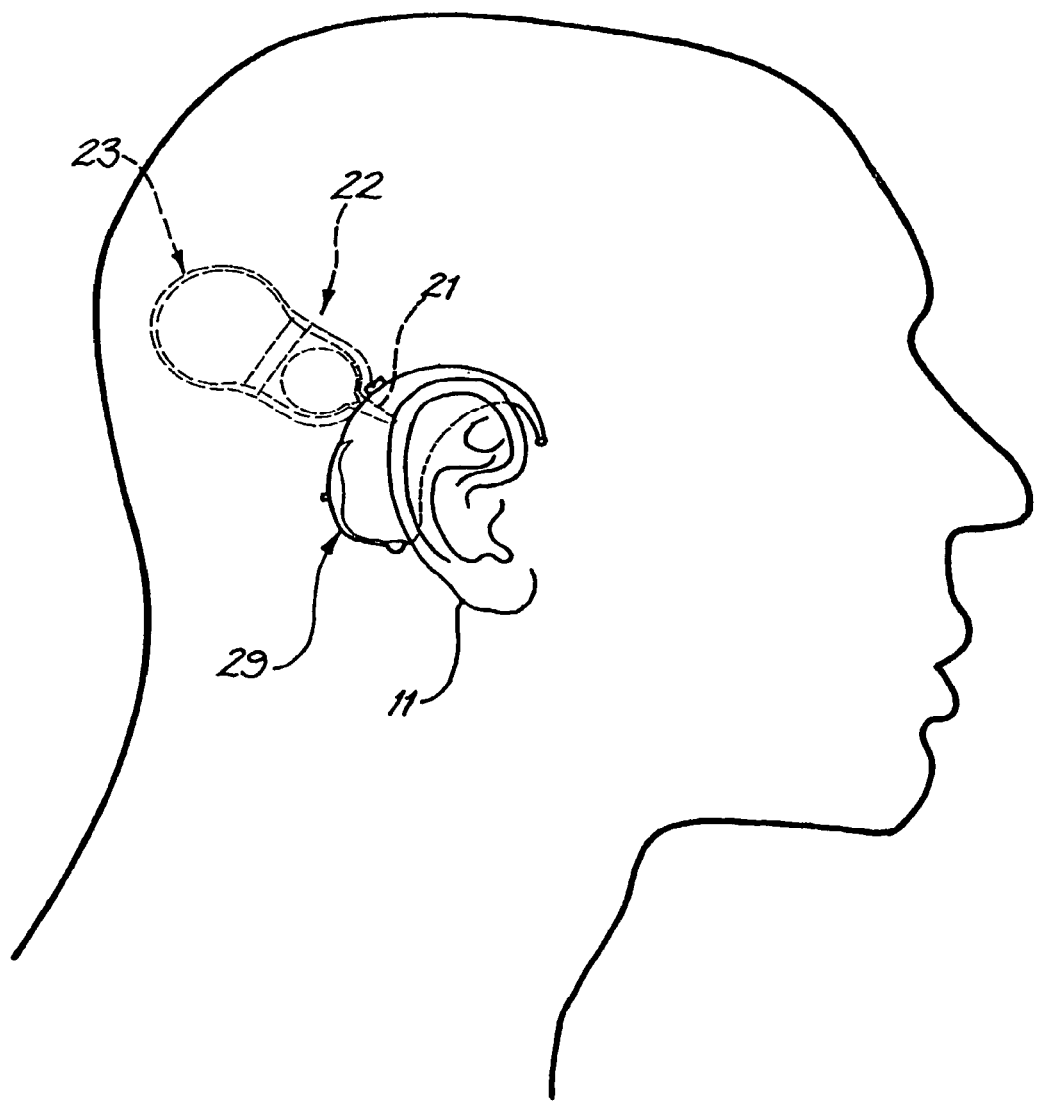

FIG. 5 shows the orientation of a typical prior art implanted stimulator unit 22 in relation to a recipient's outer ear 11 and externally worn BTE device 29. The unit 22 is positioned such that the receiver coil 23 extends towards the rear of the recipient's head, thereby allowing an external transmitter coil to be positioned over the receiver coil in a manner described in FIG. 1. The cable 21 which is connected to the implanted intracochlear electrode array is arranged at the end of the unit 22 most proximal to the cochleostomy. In such an arrangement, the stimulator unit 22 is limited in its actual orientation, with the orientation of the device, namely the direction in which the receiver coil 23 extends, being dictated by the orientation of the electrode lead cable 21 from the unit.

Figure 6:
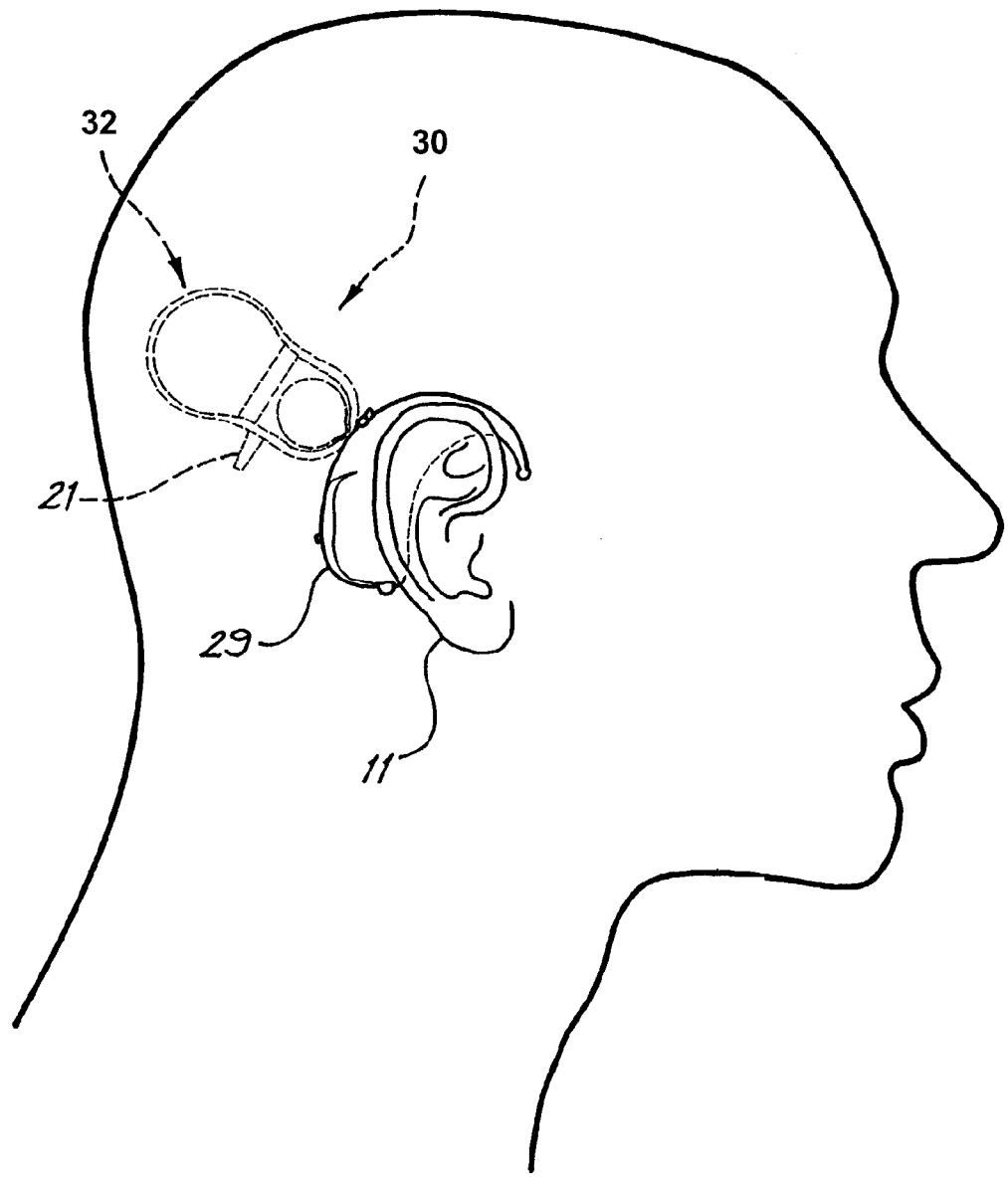
FIGS. 6 and 7 depict an external component and an implantable component of the present invention (it will be appreciated that the internal component would not be visible in use and is merely shown in these drawings to facilitate understanding of the invention)

The orientation of the implantable component of a cochlear implant system according to the present invention is shown in FIG. 6. This figure shows the stimulator unit firstly positioned in a conventional position whereby an external coil positioned remote from the BTE unit can be used to communicate with the implantable component 30 via the receiver coil 32. In this embodiment, it can be clearly seen that instead of the electrode lead cable 21 exiting the component 30 from the longitudinal end of the component 30 most proximal the cochleostomy, the electrode lead cable exits from a lateral side of the component 30. With the entire unit being symmetrical, it is therefore possible to dramatically change the orientation of the component 30.

Figure 7:
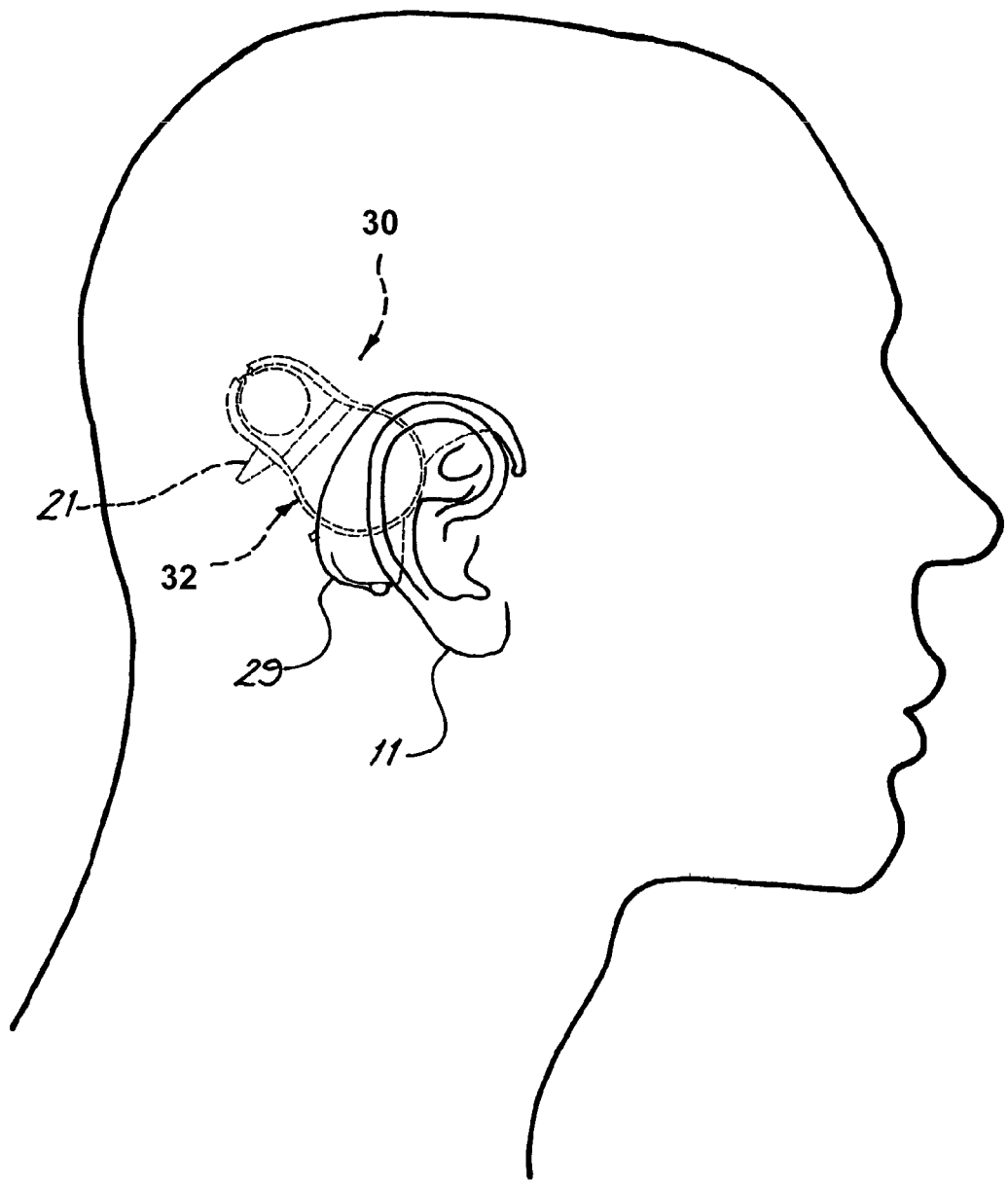

FIG. 7 shows this aspect of the present invention wherein the implantable component 30 is repositioned such that it can directly communicate with a transmitter coil (not shown in this figure) positioned in the BTE device 29. In this regard, the component 30 is rotated such that the receiver coil 32 extends behind the recipient's ear rather than towards the rear of the recipient's head, as is the case in FIGS. 5 and 6. As is shown, because the electrode lead cable 21 extends from a lateral side of the component 30, rather than a longitudinal end, such dramatic realignment is possible, which has not presently been the case in other known devices.

The present invention allows for an implanted receiver/stimulator component 30 to be implanted in a conventional manner to communicate with an external coil 24. Alignment of the external coil 24 to the internal coil is provided by a magnet 33 in the internal coil 32.

Following relatively minor surgery, the orientation of the receiver/stimulator component 30 can then be altered or even reversed, so that the component 30 can be in communication directly with a BTE device 29 having an integral transmitter coil positioned therewith without the need for a separate external coil unit.

The conventional configuration of FIG. 5 is ideal for very young children where a BTE device is not suitable and a one piece on-the-head coil linked to a small body worn processor is desirable.

When a child matures to a stage where a BTE device can be reliably worn and is looking for a more cosmetically pleasing device, the individual may undergo mild revision surgery to remove the magnet 33 from the stimulator 30 and reverse the orientation of the component 30, so that the receiver coil 32 is positioned closer towards the pinna with the receiver/stimulator package extending back towards the back of the skull, as is shown in FIG. 7. In this configuration the implant can be operated directly by a BTE processor 29 having an integral transmitter coil, without the need for a separate cable and magnetically aligned external coil. The alignment of the implanted receiver coil and the coil integral with the BTE device occurs due to the revised position of the receiver coil beneath the recipient's skin relatively close to or in alignment with the pinna of the recipient.

By having the electrode array leads exiting from the lateral edges of the implant rather than the end of the implant, the component 30 can be "flipped over" about a lateral axis to reverse the orientation of the implant without dislodging or displacing the intra-cochlear electrodes. The leads of the electrode arrays themselves preferably also have a degree of flexibility which allow them to be stretched without undergoing permanent deformation. The receiver coil 32 also preferably has a degree of flexibility, which will allow the coil, surrounded by silicone, to bend to assist in the action of reversing the implant orientation, with the receiver coil 32 being very thin so as to conform to the contour of the bone in that region of the recipient's head.

Figure 8A:
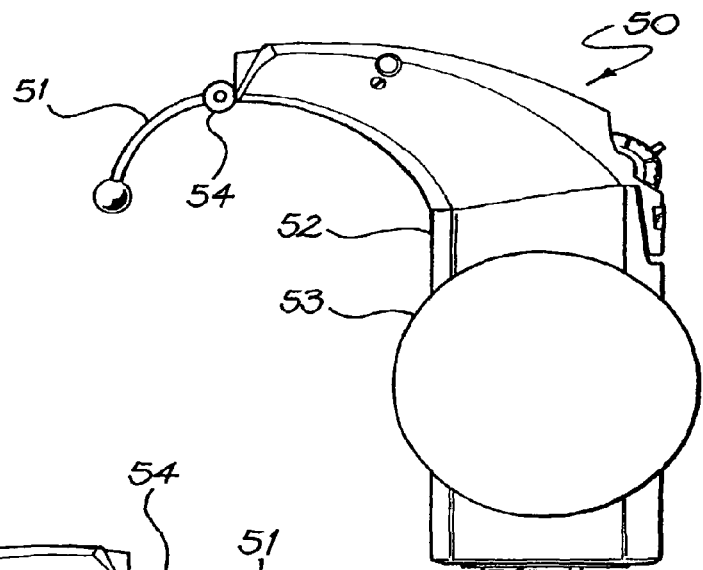
Figure 8B:
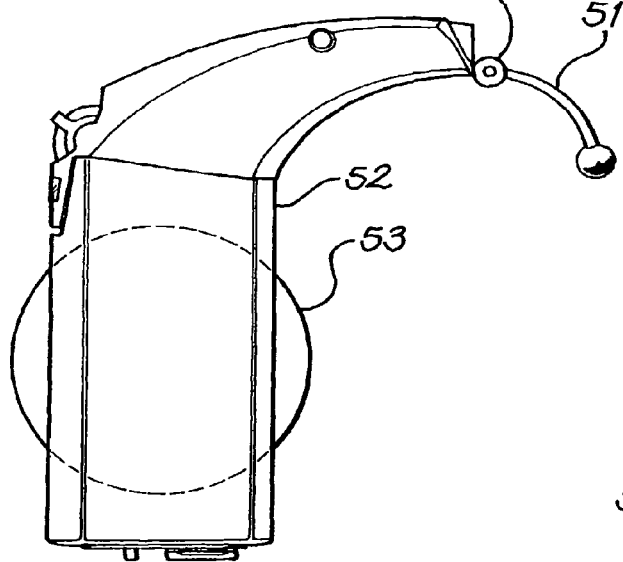
Figure 8C:
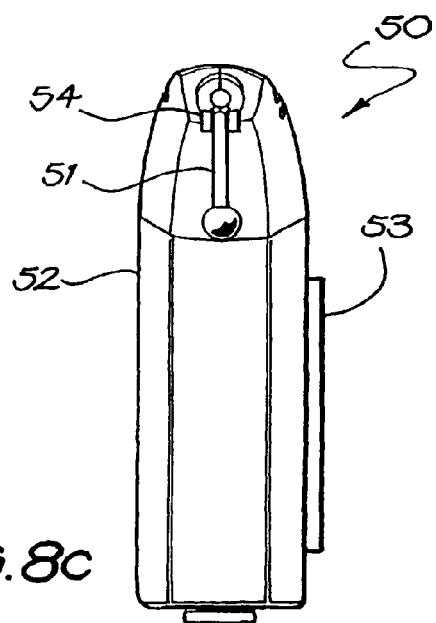

A BTE device 50 capable of being used in conjunction with the implantable component as defined herein or other forms of implantable component is shown in FIGS. 8a, 8b and 8c and 9a, 9b, and 9c. In FIGS. 8a-c, the BTE device 50 has an ear hook 51 which is capable of securing the device in place behind the ear of the user, as well as a body 52 which houses the power source and/or speech processor. A microphone can be placed on the ear hook as described with reference to FIG. 1.

A coil (here depicted as 53) is mounted integrally to the body 52 of the BTE device 50 so that when in place the coil provides a radio frequency link with the internal coil used for the system. The body 52 is, in the depicted embodiment, movably adjustable relative to the ear hook 51. As such, the position of the coil 53 can be adjusted to be brought into alignment with the position of the internal coil by adjusting the position of the body 52 relative to the ear hook.

In the depicted embodiment, the body 52 is mounted to the ear hook 51 through a universal joint 54 that allows the body 52 to move relative to the ear hook 51.

FIG. 9a-c depicts another embodiment of a supporting device according to the present invention generally as 60. In this embodiment, the device 60 utilises an ear hook element 62 to maintain the device in place behind the outer ear of the implantee. The body 61 of the device has a channel 65 on the surface of the body 61 which is designed to lie adjacent the skin behind the ear. This channel 65 is designed to receive a locating member 66 of the coil 53, to enable the position of the coil 53 to be adjusted in relation to the body of the device 61 to align with the implanted receiver coil. Whilst the channel 65 is only shown as extending along a vertical plane, it should be appreciated that this channel could be arranged in various configurations, such as zigzagged or circular to increase the variations of coil positions possible to ensure that optimum alignment is possible.

Figure 10:
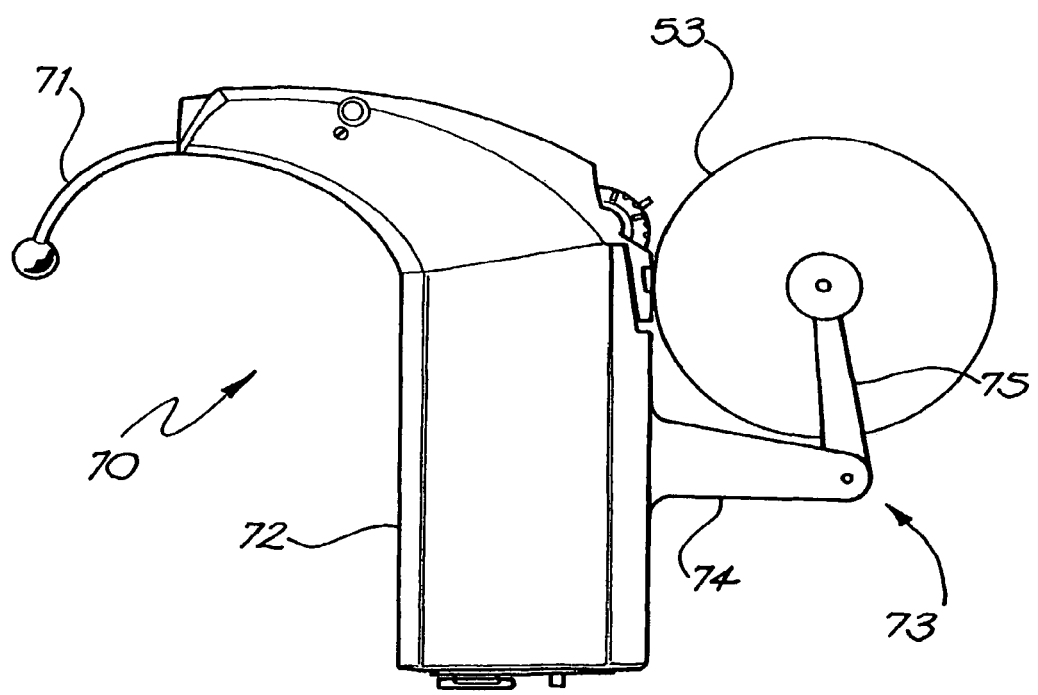
FIG. 10 is a side elevational view of another embodiment of an external component.

Yet another embodiment of a possible supporting device is depicted generally as 70 in FIG. 10. In this embodiment, the device 70 again has an ear hook element 71 and a body 72. The hook element 71 can support a microphone and the body 72 house a speech processor and/or power source as previously described. Extending rearwardly from the body 72 is an arm 73 having a first portion 74 that is rigidly mounted to the body 72 and a second portion 75 The second portion 75 is slidably mounted in a tubular orifice in the first portion 74 thereby allowing the orientation of the second portion 75 relative to the first portion 74 to be adjustable by the implantee or a third person.

A distal end of the second portion 75 supports the centre of the external coil 53. The second portion 75 can include a telescopic portion that can telescopically extend or retract to allow further finer adjustment of the coil 53

The construction of the external component provides a means of readily adjusting the orientation and position of the external coil of a cochlear implant system so as to ensure the external coil is in correct alignment with the implanted coil of the system. The system also does not require use of a magnet to ensure maintenance of alignment with attendant advantages of reduced implant size, avoidance of the need to surgically remove the magnet to undergo magnetic resonance imaging, and improved aesthetics for the external component.

Further Embodiments

According to a first aspect, the present invention is directed to a first invention comprising an implantable component of a cochlear implant system, the implantable component comprising: a housing for a stimulator unit, the stimulator unit being adapted to output one or more stimulation signals; a receiver antenna being part of a transcutaneous radio frequency link; and an electrode assembly adapted to apply electrical stimulation in accordance with the output of the stimulator unit; wherein following implantation of the electrode assembly within the cochlea, the housing and/or receiver antenna can be moved from a first implanted position to at least one second implanted position without removal of the electrode assembly from the cochlea of the recipient.

In this aspect, the electrode assembly can exit the housing from a side of the housing. On implantation, said side is preferably not the side of the housing proximal the cochleostomy. In one embodiment, the electrode assembly can extend from the housing at least partially in a downward orientation.

According to a second aspect, the present application is directed to a second invention comprising an implantable component of a cochlear implant system, the implantable component comprising: a housing for a stimulator unit, the stimulator unit being adapted to output one or more stimulation signals; a receiver antenna being part of a transcutaneous radio frequency link; and an electrode assembly that extends from said housing and is adapted to apply electrical stimulation in accordance with the output of the stimulator unit; wherein the housing has a lateral axis and is adjustable about said axis despite implantation of said electrode assembly.

In this aspect, the housing is preferably rotatable about said axis without leading to an adjustment of the position of implantation of the electrode assembly.

In a preferred embodiment of this second aspect, the electrode assembly, on implantation, extends from the housing at least initially in a downward orientation before entering the cochlea. In this aspect, the electrode assembly can exit the housing from a side of the housing through which the longitudinal axis of the housing does not pass. On implantation, said side is preferably not the side of the housing proximal the cochleostomy.

Hereinafter, the electrode assembly defined in the above aspects is referred to as the first electrode assembly.

In a preferred embodiment of both aspects, the housing has at least an upper edge and a lower edge, the first electrode assembly extending from a lower edge of the housing.

In a further embodiment, the first electrode assembly comprises a carrier member having a leading end that is insertable into a cochlea of an recipient and a trailing end distal the leading end. The elongate carrier member preferably has a plurality of electrodes mounted thereon. In one embodiment, the electrodes are mounted in a longitudinal array. Each of the electrodes have at least one wire, and possibly at least two, extending from each electrode back towards the trailing end of the carrier member.

The wires preferably extend back to the housing to at least a first feedthrough in the wall of the housing. In one embodiment, the feedthrough is positioned in the lower edge of the housing. In one embodiment, the feedthrough provides hermetic and insulated electrical connection for each wire extending from the electrode assembly into the housing of the implantable component. Each feedthrough can be formed using the method described in U.S. Pat. No. 5,046,242.

In one embodiment, the carrier member can have 22 electrodes. In another embodiment, the carrier member can have 30 electrodes. It is envisaged that the carrier member can have any number of electrodes as so desired, according to the intended purpose of the device. The electrodes are preferably formed from a biocompatible electrically conducting material, such as a suitable metal, such as platinum.

The elongate carrier member is preferably formed from a resiliently flexible material. In one embodiment, the carrier member can be preformed from a plastics material with memory.

In a preferred embodiment, the orientation of the carrier member as it is firstly inserted through a cochleostomy into the cochlea is preferably substantially straight. More preferably, the implantable orientation is straight. Following completion of implantation, the carrier member preferably adopts a spirally curved configuration that at least partially matches the spiral nature of the scala tympani of the human cochlea. The carrier member is preferably pre-formed with this spiral configuration and is then straightened either during manufacture and packaging of the device or prior to implantation.

In a preferred embodiment, the elongate carrier member is formed from a suitable biocompatible material. In one embodiment, the biocompatible material can be a silicone, such as a flexible silicone elastomer-Silastic. Silastic MDX 4-4210 is an example of one suitable silicone for use in the formation of the elongate member. In another embodiment, the elongate carrier member can be formed from a polyurethane or similar material.

In a preferred embodiment, the implantable component further comprises a second electrode assembly. While it can be envisaged that the second electrode assembly could also be insertable in the cochlea, it is preferred that the second electrode assembly has one or more electrodes thereon and is adapted to be implantable external of the internal passages of the cochlea.

The second electrode assembly preferably extends from the housing, once implanted, at least initially in an upward orientation. In a further embodiment, the second electrode assembly preferably extends from the upper edge of the housing. This second electrode assembly is typically implanted external of the cochlea in the muscle surrounding the head of the user. In this instance, the electrode assembly is referred to as an extra-cochlear electrode assembly and this allows the stimulation method known as monopolar stimulation to be performed. In monopolar stimulation, the stimulation passes between an intracochlear and an extracochlear electrode, providing for a wide current spread.

The second electrode assembly preferably has one or more of the features defined herein in relation to the first intracochlear electrode assembly. In a preferred embodiment, the second electrode assembly has one or two electrodes thereon.

In a further embodiment, the housing is preferably implantable in a recess of the temporal bone adjacent the ear of the recipient that is receiving the output of the implant system. The housing is preferably formed from a biocompatible material or has a biocompatible coating. The housing can be coated with a layer of silicone or parylene.

The receiver antenna preferably comprises a wire antenna coil. The antenna coil can be comprised of at least one, and preferably at least three, turns of electrically insulated platinum or gold wire tuned to parallel resonance by a capacitor internal to the housing. The electrical insulation of the receiver antenna can be provided by a thin, flexible silicone molding and/or silicone or polyurethane tubing.

The receiver antenna is preferably external of the housing of the stimulator unit. The molding of the receiver antenna can also extend around at least some of the housing of the stimulator unit. The connection between the housing and the receiver antenna is preferably such that repositioning of the housing also results in repositioning of the antenna. The antenna is preferably relatively quite thin enabling the antenna, if desired, to be implanted behind the ear. Electrical connection between the antenna and componentry of the implantable componentry within the housing can be provided by two hermetic and electrically insulated ceramic feedthroughs or an electrical conductor. The ceramic feedthroughs can be formed using the method described in abovementioned U.S. Pat. No. 5,046,242.

The receiver antenna preferably has a maximum thickness that is less than the maximum thickness of the housing. In one embodiment, the antenna preferably has a thickness of about 2.5 mm whereas the housing preferably has a maximum thickness of about 3.5 mm. Where a coil, the coil preferably has a diameter of about 25 mm.

The receiver antenna of the implantable component preferably acts as part of a radio frequency (RF) link to allow transcutaneous bidirectional data transfer between the implantable component and an external component of the system. The link preferably further comprises an external antenna that is able to be aligned with the position of the implantable receiver antenna. The radio frequency signals can be modified to encode data using the method described in U.S. Pat. No. 5,741,314. While described as a receiver antenna, the receiver antenna can preferably also transmit signals back to the transmitter antenna which receives the signals for the purpose of telemetry from the implanted receiver/stimulator unit.

The link between the two antennae also provides a means of powering the componentry of the internal component. In the case where the implantable component further has an on-board or implantable power source, such as a rechargeable battery, the link can provide a means of inductively charging the battery when required.

When implanted, the housing preferably contains, in addition to the stimulator unit, a receiver unit. The receiver unit is preferably adapted to receive signals from an external component that comprises at least a controller. The controller is, in use, preferably mounted external to the body of the recipient such that the signals are transmitted transcutaneously through the skin of the recipient.

The external controller can have a housing for a speech processor adapted to receive signals output by a microphone. During use, the microphone can be mounted in the housing that is preferably supported on the pinna of the recipient. Other suitable locations for the microphone and/or the housing can be envisaged, such as a lapel of the recipient's clothing.

The speech processor encodes the sound detected by the microphone into a sequence of electrical stimuli following given algorithms, such as algorithms already developed for cochlear implant systems. The encoded sequence is transferred to the implanted receiver/stimulator unit mina the transmitter and receiver antennae. The implanted receiver/stimulator unit demodulates the modulated signal and allocates the electrical pulses to the appropriate attached electrode by an algorithm which is consistent with the chosen speech coding strategy.

The external controller preferably further comprises a power supply. The power supply can comprise one or more rechargeable batteries. The transmitter and receiver antennae are used to provide power via transcutaneous induction to the implanted receiver/stimulator unit and the electrode array.

In a further embodiment, the receiver coil can be disposed about a magnet. The magnet, when present, is preferably centrally disposed in the receiver coil.

When present, the magnet can be used to hold and align an external coil mounted to the outside of the head of the recipient. To achieve, this a ferromagnetic material or another magnet arranged to experience an attraction force to the magnet within the receiver coil can be positioned in a central location within the external coil.

In one embodiment, the magnet can be removable from its location within the receiver coil.

In a preferred embodiment, the receiver antenna can be flexed or deformed relative to the housing. Still further, the casing can preferably rotate about a lateral axis despite the first and/or second electrode assemblies being connected thereto and in an implanted position within the recipient. In this regard, a surgeon, if desired, can rotate the housing about said lateral axis when a change in location of the receiver antenna is required within the head of the recipient. By rotating the housing about a lateral axis, the lower edge of the housing preferably remains the lower edge once the housing has been rotated.

While the implant system can rely on external componentry, in another embodiment, the controller, including the microphone, speech processor and power supply can also be implantable. In this embodiment, the controller can be contained within a hermetically sealed housing or the housing used for the stimulator unit.

To facilitate the adjustment in orientation of the housing about the lateral axis, the housing can be fabricated from a resiliently flexible material that facilitates the change in orientation. For example, a region adjacent one or both ends or one or both of the upper and lower sides can be deformed, bent or at least partially rolled up to facilitate the change in orientation of the housing in a surgical environment and despite the first and/or second electrode assemblies remaining in their originally implanted positions.

In yet a further embodiment, the change in position and/or orientation of the housing can result in the receiver antenna moving from an implanted position that is aligned with or at least close to the position of the outer ear or pinna to a more distal location or vice versa.

This property of being rotatable about a lateral axis provides a cochlear implant system that can adjust to growth in dimensions of the recipient's head as can be expected as a baby grows into childhood and then further into adulthood.

For example, for a baby or young child, there are a number of advantages in utilizing a magnetic alignment system. In particular, the magnet serves to hold the external coil in the appropriate alignment with the internal coil which is important as such an recipient is unlikely to notice when the external coil has been dislodged or be physically unable to appropriately reposition the external coil on noticing dislodgment. As such, the magnetic alignment system serves to preferably prevent any such dislodgment. To use a magnetic alignment system, it is preferred that the external coil be positioned at least some distance from the external componentry. To accommodate this known requirement, the implantable component of the present invention would be firstly preferably implanted such that the implanted coil is at said distal location relative to the outer ear of the recipient that is likely to be supporting the external componentry.

As the child grows, the option is available with this implantable component for the recipient to undergo a further surgery in which the housing of the component is rotated about its lateral axis so bringing the receiver coil to a position more adjacent the position of the outer ear or pinna of the recipient. During such a surgery, any magnet present in the receiver coil is preferably removed. In this case, alignment of the respective coils is provided by simply having the receiver coil in alignment with the position of the external coil supported on the external component. In this case, the external transmitter coil is preferably tucked behind the pinna of the outer ear and so is far less noticeable to other persons. Indeed, for a person with long and/or thick hair that extends over the ears, the presence of the external component may not be noticeable to at least a casual inspection.

In the above aspects, the implantable component can be implanted with either a first face or a second face adjacent or nearest the skin of the recipient without there being any significant or indeed no change in the operation of the component. In this way, a single implantable component can be used in conjunction with either the left or right ear and yet still be repositionable or rotatable as defined herein. In this embodiment, there is no need for the surgeon to ensure that a particular face of the implantable component is adjacent the skin as the implant operates irrespective of its orientation or position of implantation.

In this and other embodiments, the implantable component is preferably at least substantially symmetrical about a longitudinal plane. In a still further embodiment, the implantable component can be at least substantially symmetrical about a lateral plane.

According to a third aspect, the present application is directed to a third invention comprising an implantable component of a cochlear implant system, the implantable component comprising: a housing for a stimulator unit, the stimulator unit being adapted to output one or more stimulation signals; a receiver antenna being part of a transcutaneous radio frequency link; and an electrode assembly adapted to apply electrical stimulation in accordance with the output of the stimulator unit; wherein the housing has a longitudinal plane and is at least substantially symmetrical about said plane.

In this aspect, the housing is preferably symmetrical about said plane. In another embodiment, the housing preferably also has a lateral plane and is at least substantially symmetrical about this lateral plane. In yet another embodiment, the receiver antenna is also symmetrical about the longitudinal and/or lateral plane.

According to a fourth aspect, the present application is directed to a fourth invention comprising an implantable component of a cochlear implant system, the implantable component comprising: a housing for a stimulator unit, the stimulator unit being adapted to output one or more stimulation signals; a receiver antenna being part of a transcutaneous radio frequency link; and an electrode assembly adapted to apply electrical stimulation in accordance with the output of the stimulator unit; wherein the housing has a lateral plane and is at least substantially symmetrical about said plane.

In this aspect, the housing is preferably symmetrical about said lateral plane.

According to a fifth aspect, the present application is directed to a fifth invention comprising a method of adjusting the implanted position of a housing of an implantable component of a cochlear implant system, the method comprising the steps of: accessing the site of implantation; repositioning the housing or rotating the housing about a lateral axis of the housing; and closing the implantation site.

In this aspect, the housing preferably has the features of the housing as defined herein in relation to the first to fourth aspects.

On initial implantation, the implantable component is preferably removably implanted within a recess in the mastoid bone of the recipient. The component is preferably held in place using one or more fastening devices that hold the component to the mastoid bone. In one embodiment, the fastening devices can comprise one or more sutures extending from tie down members on the housing to the bone. In another embodiment, the fastening devices can comprise bone screws that pass through receiving members of the housing and into the mastoid bone. Whatever fastening devices is employed, the fastening devices is preferably removable to allow the component to he rotated as described herein when desired.

According to a sixth aspect, this application is directed to a sixth invention comprising an external component of a cochlear implant system, the external component comprising:
a support for mounting to the ear of an recipient; and an external signal transmitter antenna;
wherein the signal transmitter antenna is movably mounted to at least a portion of the support.

In one embodiment of this aspect, the external transmitter antenna comprises a transmitter coil. The transmitter coil is preferably adapted to provide in combination with an implanted receiver antenna a transcutaneous radio frequency (RF) link between the external component of the cochlear implant system and an implanted component thereof. In one embodiment, the implanted component can have the features according to the first to fourth aspects defined herein including the embodiments thereof.

In a still further embodiment, the support comprises a housing having an ear hook member. The member preferably extends forwardly from the housing and is adapted, when used, to sit over the outer ear of the recipient. On mounting to the outer ear, the housing apart from the ear hook member is preferably positioned behind the outer ear or pinna.

In one embodiment of the sixth aspect, the external transmitter antenna can be movably mounted to the housing of the support. In this embodiment, the transmitter antenna can be mounted to a bracket that is slidably mounted to the housing. In one embodiment, the transmitter antenna can be slidably adjustable up and down the housing. In one embodiment, the transmitter antenna can be slidably adjustable along or parallel to a longitudinal axis thereof. In addition to or instead of the longitudinal movement, the transmitter antenna can be movably adjustable across the housing. In this embodiment, the transmitter antenna can slidably move across the housing along or parallel to a lateral axis of the housing.

In a still further embodiment, the housing of the external component can be relatively movably mounted to the ear hook member. In this embodiment, the external component can be relatively slidably movable with respect to the ear hook member. In this case, the transmitter antenna can be fixed or relatively movably mounted to the housing or the ear hook member.

In addition to being slidably movable in one direction, the housing can be relatively adjustable in other orientations to the ear hook member.

In yet another embodiment, the external transmitter antenna can be mounted to an arm extending outwardly from the housing. In a preferred embodiment, the arm can have a first non-movable portion extending rearwardly from the housing and a second movable portion adapted to articulate through a joint with the first portion. In one embodiment, the second portion preferably extends generally upwardly from the joint with the first portion. The external transmitter antenna is preferably supported at a distal end of the second portion of the arm. The second portion can include a telescopic portion that can telescopically extend or retract to provide further finer adjustment of the position of the transmitter antenna.

In a preferred embodiment, the joint is a universal joint so allowing freedom of movement of the second portion relative to the first portion. The joint is preferably adapted to only move on application of hand pressure to the movable portion of the arm. As such, the second portion is preferably hand adjustable by the recipient or a third person but is resistant to inadvertent movement caused by movement of the head or relatively soft knocks.

In each of the above embodiments of the sixth aspect, the support can further comprise a locking mechanisms adapted to lock the bracket, the housing, or the second portion of the arm in a desired position. In one embodiment, the locking mechanism can comprise a grub screw that passes through the relatively movable portion of the support and can be hand turned to frictionally engage another portion of the support thereby preventing further movement.

In the sixth aspect, the housing of the external component preferably houses a speech processor adapted to receive signals output by a microphone. In a preferred embodiment, the microphone can be mounted to the housing or the ear hook member Other suitable locations for the microphone and/or the housing for the speech processor can be envisaged, such as a lapel of the implantee's clothing.

The speech processor encodes the sound detected by the microphone into a sequence of electrical stimuli following given algorithms, such as algorithms already developed for cochlear implant systems. The encoded sequence is transferred to the implanted receiver/stimulator unit using the transmitter and receiver coils. The implanted receiver/stimulator unit demodulates the modulated signal and allocates the electrical pulses to the appropriate attached electrode by an algorithm which is consistent with the chosen speech coding strategy.

The external component of the sixth aspect preferably further comprises a power supply. The power supply can comprise one or more primary cells or rechargeable batteries. The transmitter and receiver antennae are used to provide power via transcutaneous induction to the implanted receiver/stimulator unit and the electrode array.

As the external antenna is preferably positioned on the support having an ear hook member, it will be understood that the external antenna will typically be positioned immediately behind or close to the outer ear. The implanted antenna is preferably positioned on implantation to be alignable with an external antenna in this position. The movable mounting of the external transmitter to at least a portion of the support preferably allows the implantee or a third person to adjust the position of the external antenna to achieve optimum alignment of the external antenna to the implanted antenna.

This property of being adjustable provides a cochlear implant system that can adjust to growth in dimensions of the implantee's head as can be expected as a baby grows into childhood and then further into adulthood.

Still further, this property allows an implantee to use a more discreet magnetless system with the majority of the external component positioned behind the outer ear of the implantee and without the need for a separate antenna and associated leads which is currently the case. As such, the external component is far less noticeable to other persons. Indeed, for a person with long and/or thick hair that extends over the ears, the presence of the external component may not be noticeable to casual inspection.

According to a still further aspect, the present invention is a cochlear implant system capable of operating in both a magnet and a magnetless manner and comprising: an implantable stimulator unit that is implantable in a first and at least a second orientation in the head of the recipient; an external controller unit capable of being 'worn behind the ear of the recipient; and a transmission system capable of transmitting signals from the external controller unit to the implantable stimulator unit; wherein when said implantable stimulator unit is implanted in a first orientation said transmission system is positioned distal from said external controller unit being worn behind the outer ear of the recipient; and wherein when the implantable stimulator unit is in said second orientation, said transmission system is positioned proximal or integral with said external controller being worn behind the outer ear of the recipient.

In this aspect, the stimulator unit can be part of an implantable component as defined herein elsewhere. The external controller unit can also be part of an external component as defined herein elsewhere.

When in said first orientation, magnetic attraction is preferably used to provide and retain alignment between the implanted and external antennae of the transmission system.

When in the second orientation, appropriate mounting of the external antenna on the external component when mounted to the ear of the recipient provides the necessary alignment with the implanted antenna.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A cochlear implant system comprising:
    (a) an external component comprising:
        a support configured to house electronic components and to be mounted to an outer ear of a recipient; and
        an external antenna configured to provide one or more of power and data signals from the electronic components to an implantable component of the cochlear implant system,
        wherein the external antenna is mounted to the support such that the external antenna is moveable relative to at least a portion of the support; and
    (b) an implantable component comprising:
        an implantable housing configured to be implanted in a recipient and having a receiver coil and a receiver/stimulator package that are substantially aligned along a longitudinal axis, wherein the receiver/stimulator package is configured to output stimulation signals and is disposed outside a circumference of the receiver coil; and
        a first electrode assembly having contiguous first and second regions, wherein the first region extends from the housing along a lateral axis substantially perpendicular to the longitudinal axis, wherein the lateral axis extends through the housing between a center of the receiver coil and a center of the receiver/stimulator package, and wherein the second region is configured to be at least partially implanted in a cochlea of the recipient,
        wherein the housing and the first region are configured such that, when the second region is disposed in the cochlea, the housing is rotatable about a rotational axis substantially parallel with the lateral axis, and wherein the housing is rotatable such that the second region remains substantially stationary during the rotation.

2. The cochlear implant system of claim 1, wherein the support comprises:
an ear hook configured to rest over an outer ear of the recipient when the support is mounted to the recipient; and
a housing configured to house the electronic components, wherein the external antenna is mounted to the exterior of the housing.

3. The cochlear implant system of claim 2, wherein the housing is moveably connected to the ear hook such that the external antenna is movable relative to the ear hook.

4. The cochlear implant system of claim 2, wherein the external antenna is moveably mounted to the housing.

5. The cochlear implant system of claim 4, wherein the external antenna comprises a locating member and the housing comprises a channel configured to receive the locating member such that the locating member may be moved relative to the housing within the channel.

6. The cochlear implant system of claim 2, wherein the external antenna is mounted to an arm that extends outwardly from the housing, the arm comprising:
a first portion rigidly mounted to the housing; and
a second portion connected to the external coil and movably mounted to the first portion such that the external coil is movable relative to the housing.

7. The cochlear implant system of claim 1, wherein the support further comprises a locking mechanism configured to prevent movement of the external antenna relative to the support when in a locked configuration.

8. The cochlear implant system of claim 1, wherein the external antenna comprises an external coil configured to communicate transcutaneously with an implantable coil of the implantable component via radio frequency (RF) signals.

9. A cochlear implant system comprising:
an implantable component comprising a receiver coil comprising:
an implantable housing configured to be implanted in a recipient and having a receiver coil and a receiver/stimulator package that are substantially aligned along a longitudinal axis, wherein the receiver/stimulator package is configured to output stimulation signals and is disposed outside a circumference of the receiver coil; and
a first electrode assembly having contiguous first and second regions, wherein the first region extends from the housing along a lateral axis substantially perpendicular to the longitudinal axis, wherein the lateral axis extends through the housing between a center of the receiver coil and a center of the receiver/stimulator package, and wherein the second region is configured to be at least partially implanted in a cochlea of the recipient,
wherein the housing and the first region are configured such that, when the second region is disposed in the cochlea, the housing is rotatable about a rotational axis substantially parallel with the lateral axis, and wherein the housing is rotatable such that the second region remains substantially stationary during the rotation; and
an external component comprising:
a support including an ear hook configured to be mounted to an outer ear of the recipient and a housing configured to house electronic components; and
an external antenna configured to provide one or more of power and data signals from the electronic components to the receiver coil,
wherein the external antenna is mounted to the support such that the external antenna is moveable relative to one or more of the ear hook and the housing.

10. The cochlear implant of claim 9, wherein the ear hook is configured to rest over the outer ear of the recipient when the support is mounted to the recipient, the external antenna is mounted to the exterior of the housing, and the housing is moveably connected to the ear hook such that the external antenna is movable relative to the ear hook.

11. The cochlear implant of claim 9, wherein the external antenna comprises a locating member and the exterior of the housing comprises a channel configured to receive the locating member such that the locating member may be moved relative to the housing within the channel.

12. The cochlear implant of claim 9, wherein the external antenna is mounted to an arm that extends outwardly from the housing, the arm comprising:
a first portion rigidly mounted to the housing; and
a second portion connected to the external coil and movably mounted to the first portion such that the external coil is movable relative to the housing.

13. The cochlear implant of claim 9, wherein the implantable housing is rotatable between a first implanted orientation in which the receiver/stimulator package is disposed closer to the outer ear of the recipient than is the receiver coil, and a second implanted orientation in which the receiver coil is disposed closer to the outer ear than is the receiver/stimulator package.

14. A method of adjusting a cochlear implant system comprising an implantable component and an external component, the implantable component including an implantable housing and a receiver coil, and the external component including a support and an external antenna mounted to the support, wherein the implantable housing has therein the receiver coil and a receiver/stimulator package substantially aligned along a longitudinal axis, wherein the receiver/stimulator package is configured to output stimulation signals and is disposed outside a circumference of the receiver coil, and wherein the implantable component further comprises:
a first electrode assembly having contiguous first and second regions, wherein the first region extends from the housing along a lateral axis substantially perpendicular to the longitudinal axis, wherein the lateral axis extends through the housing between a center of the receiver coil and a center of the receiver/stimulator package, and wherein the second region is configured to be at least partially implanted in a cochlea of the recipient,
wherein the housing and the first region are configured such that, when the second region is disposed in the cochlea, the housing is rotatable about a rotational axis substantially parallel with the lateral axis, and wherein the housing is rotatable such that the second region remains substantially stationary during the rotation;
the method comprising:
accessing a site at which the implantable component is implanted in the recipient;
removing a magnet from the implantable housing;
rotating the implantable housing from a first implanted orientation in which the receiver/stimulator package is disposed closer to the outer ear of the recipient than is the receiver coil to a second implanted orientation in which the receiver coil is disposed closer to the outer ear than is the receiver/stimulator package; and
closing the implantation site; and moving the external antenna relative to at least a portion of the support such that, when the external component is mounted to a recipient's outer ear, the external antenna is substantially aligned with the receiver coil implanted in the recipient; and locking the external antenna to the support, using a locking mechanism, to prevent the external antenna from moving relative to the support.

15. The method of claim 14, wherein said support comprises an ear hook and a housing configured to house one or more electronic components, the external antenna is mounted to the exterior of the housing, and said moving the external antenna relative to at least a portion of the support comprises:

moving the housing relative to the ear hook.

16. The method of claim 14, wherein the external antenna comprises a locating member and the support comprises a channel configured to receive the locating member, and said moving the external antenna relative to at least a portion of the support comprises:

moving the locating member within the channel.

17. The method of claim 14, wherein the external antenna is mounted to an arm that extends outwardly from the support, the arm comprises a first portion rigidly mounted to the exterior of the housing and a second portion connected to the external coil, and said moving the external antenna relative to at least a portion of the support comprises:

moving the second portion relative to the first portion.

18. A method of adjusting a cochlear implant system comprising an implantable component and an external component, the implantable component comprising an implantable housing having therein the receiver coil and a receiver/stimulator package substantially aligned along a longitudinal axis, wherein the receiver/stimulator package is configured to output stimulation signals and is disposed outside a circumference of the receiver coil, and wherein the implantable component further comprises:

a first electrode assembly having contiguous first and second regions, wherein the first region extends from the housing along a lateral axis substantially perpendicular to the longitudinal axis, wherein the lateral axis extends through the housing between a center of the receiver coil and a center of the receiver/stimulator package, and wherein the second region is configured to be at least partially implanted in a cochlea of the recipient, the method comprising:

rotating the housing about a rotational axis substantially parallel with the lateral axis such that the second region remains disposed in the cochlea and remains substantially stationary during the rotation.

19. The method of claim 18, further comprising rotating the implantable housing from a first implanted orientation in which the receiver/stimulator package is disposed closer to an outer ear of a recipient than is the receiver coil to a second implanted orientation in which the receiver coil is disposed closer to the outer ear than is the receiver/stimulator package.

* * * * *